United States Patent [19]
Mattingly

[11] Patent Number: 5,616,298
[45] Date of Patent: *Apr. 1, 1997

[54] 5(6)-METHYL SUBSTITUTED FLUORESCEIN DERIVATIVES

[75] Inventor: Phillip G. Mattingly, Grayslake, Ill.

[73] Assignee: Abbott Laboratories, Abbott Park, Ill.

[*] Notice: The term of this patent shall not extend beyond the expiration date of Pat. No. 5,496,925.

[21] Appl. No.: 445,962

[22] Filed: May 22, 1995

Related U.S. Application Data

[62] Division of Ser. No. 421,143, Apr. 13, 1995, Pat. No. 5,496,925, which is a continuation of Ser. No. 260,578, Jun. 16, 1994, abandoned, which is a division of Ser. No. 859,775, Mar. 30, 1992, Pat. No. 5,352,803.

[51] Int. Cl.$^6$ .......................... A61K 35/14; C07K 14/00; C07D 311/82; G01N 33/53
[52] U.S. Cl. .......................... 422/61; 530/350; 530/807; 530/387.1; 549/223; 436/164; 436/172; 436/800
[58] Field of Search .......................... 530/350, 807, 530/408, 387.1, 409, 410; 549/220, 223; 435/4, 1.1; 436/800, 164, 172; 422/61

[56] References Cited

U.S. PATENT DOCUMENTS

| | | | |
|---|---|---|---|
| 4,329,461 | 5/1982 | Khanna et al. | 544/375 |
| 4,476,229 | 10/1984 | Fino et al. | 436/500 |
| 4,640,893 | 2/1987 | Mangel et al. | 435/23 |

FOREIGN PATENT DOCUMENTS

| | | |
|---|---|---|
| 0264797 | 4/1988 | European Pat. Off. . |
| 0297303 | 1/1989 | European Pat. Off. . |
| 0455058 | 11/1991 | European Pat. Off. . |
| 0473961 | 9/1992 | European Pat. Off. . |
| 0533200 | 3/1993 | European Pat. Off. . |
| 9304192 | 3/1993 | European Pat. Off. . |

*Primary Examiner*—Jeffrey Snay
*Attorney, Agent, or Firm*—John F. Levis

[57] ABSTRACT

5(6)-methyl substituted fluorescein derivatives and a process for producing 5(6)-methyl substituted derivatives. Also provided are methods for these utilizing these derivatives as indicator reagents in assays for analytes, indicator reagents which comprise specific binding members attached to these derivatives and test kits which contain these derivatives.

1 Claim, 1 Drawing Sheet

5(6)-METHYL SUBSTITUTED FLUORESCEIN DERIVATIVES

This application is a Divisional of U.S. Ser. No. 08/421,143 filed Apr. 13, 1995, now U.S. Pat. No. 5,496,925; which is a Continuation of U.S. Ser. No. 08/260,578 filed Jun. 16, 1994 and now abandoned; which is a Divisional U.S. Ser. No. 07/859,775, filed Mar. 30, 1992, now U.S. Pat. No. 5,352,803.

BACKGROUND ART

This invention relates generally to fluorescein derivatives, and more particularly, relates to 5(6)-methyl substituted fluorescein derivatives and their production by the reduction of 5(6)-carboxyfluorescein to 5(6)-methyl substituted fluorescein.

There are numerous fluorescein derivatives that have functional groups which are suitable for reaction with other molecules. Many of these derivatives have been used commercially in the production of tracers for analytical applications which range from the probing of cell functions to the monitoring of the level of one or more drugs in physiological test samples. See, for example, C. Dive et al., *Molecular and Cellular Probes* 2:31 (1988); M. L. Graber et al., *Anal. Biochem*, 156:202 (1986); P. J. Brynes et al., U.S. Pat. No. 4,869,132; and N. Y. Wang et al., European Patent Application Publ. No. EP264797 (1988). Examples of such applications include the Fluorescence Polarization Immunoassay (FPIA) for use on commercially available instruments, such as the Abbott $AD_x$® instrument and the Abbott $TD_x$® instrument (available from Abbott Laboratories, Abbott Park, Ill.. These derivatives include 5- and 6-carboxyfluorescein, 5- and 6-aminofluorescein and 4'-aminomethylfluorescein(M. T. Shipchandler, et. al., *Anal. Biochem*, 162:89 (1987). Of these, the 5- and 6-aminofluorescein compounds are the most difficult with which to work, since the amino group is not very nucleophilic. This difficulty is an expected consequence of the amino group being directly bound to the deactivating aromatic ring. The compound 4'-aminomethylfluorescein (4'-AMF) was an earlier attempt to solve this problem by adding a methylene group between the amino group and the aromatic ring. This addition succeeded in restoring normal amino group reactivity of 4'-AMF. However some 4'-AMF derivatives have been found to be unstable under the conditions of long term storage in aqueous buffers. Possibly this instability is due to a retro-Mannich reaction or subsequent elimination of the amino group (H. O. House, *Modern Synthetic Reactions*, 2nd Ed., 1972, pp 654–660). Additionally, the preparation and purification of 4'-AMF is tedious.

Martin et. al., (*Cytometry* 12:184–187 [1991]) report a preparation of 5-chloromethyl fluorescein diacetate by the halogenation of 5-methylfluorescein diacetate without including any experimental details. Also, Peerce et. al. (*J. Biol. Chem.* 260 (10):6026–31 [1985]) report a methyl substituted fluorescein derivative with the given structure:

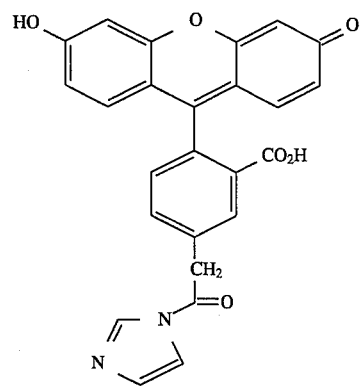

However, the experimental procedure reported by Peerce et al. would indicate that the compound was actually of the following structure:

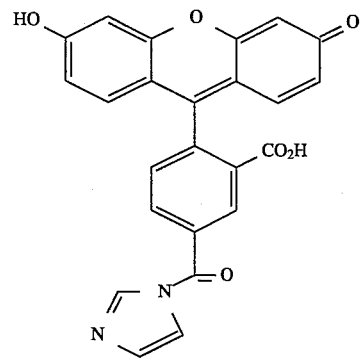

Khana et. al. (U.S. Pat. No. 4,439,365) disclose xanthene compounds of the following structures, but again offer no experimental details:

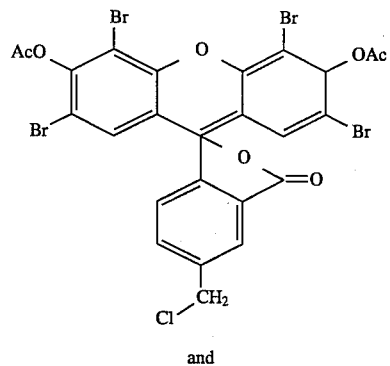

and

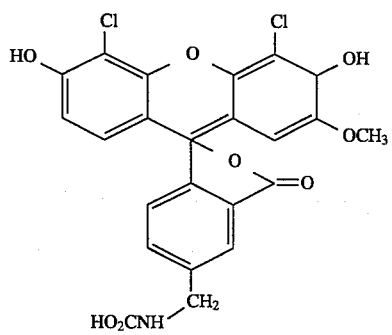

The reduction of 5(6)-carboxyfluorescein derivatives is not known. However, in general, carboxylic acid derivatives (i.e., free acids, metal salts, amides, esters, acid halides, etc.) may be reduced by a variety of methods. These methods have been reviewed extensively in the literature. See, for example, H. C. Brown, *Boranes in Organic Chemistry*, Cornell University Press (1972); and C. F. Lane, "Reductions of Organic Compounds with Diborane," *Chemical Reviews* 76:773–799 (1976). Also, the reduction of activated carboxylic acids to alcohols with sodium borohydride has been described. K. Ramasamy et al., *Synthesis:* 42 (1982).

The present invention solves the problem of amino reactivity at the 5 or 6 position by adding a methylene group between it and the aromatic ring. Additionally, the novel processes employed results in the availability of novel and useful derivatives available for use in tracer synthesis, and for use in analytical assays.

SUMMARY OF THE INVENTION

The present invention provides fluorescein derivatives of the following formulas:

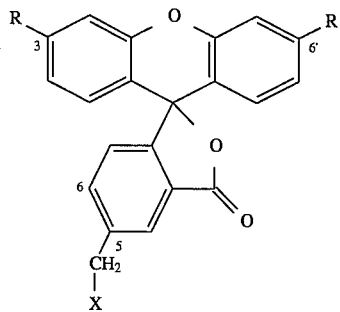

FORMULA I and

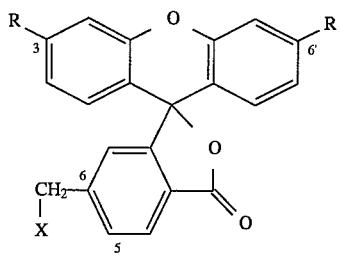

FORMULA II wherein R is selected from the group consisting of hydroxy (—OH), and protected hydroxy (—OZ); and wherein X is selected from the group consisting of hydroxy (—OH), protected hydroxy (—OZ), amine (—NH$_2$), protected amine (—NH$_m$Z'$_{2-m}$), thiol (—SH), protected thiol (—SZ"), a leaving group, a Michael acceptor, phosphoramidite, phosphonate and a linking group.

Hydroxyl groups are routinely protected as alkyl or aryl ethers (Z=alkyl, aryl, alkenyl), silyl ethers (Z=silyl), esters (Z=acyl), carbonates (Z=—C(=O)—O-alkyl, —C(=O)—O-aryl,—C(=O)—O-alkenyl) and carbamates (Z=—C(=O)—NH-alkyl,—C(=O)—NH-aryl, —C(=O)—NH-alkenyl). Amino groups are routinely protected as carbamates (Z'=—C(=O)—O-alkyl, —C(=O)—O-aryl, —C(=O)—O-alkenyl), biscarbamates (m=0; Z'=—C(=O)—O-alkyl, —C(=O)—O-aryl, —C(=O)—O-alkenyl), amides (Z'=—C(=O)-alkyl, —C(=O)-aryl, —C(=O)-alkenyl), cyclic imides (m=0; Z'=phthaloyl), N-benzyl derivatives (Z'=—CH($_n$)aryl($_{3-n}$), n=1–3), imine derivatives sulfenyl derivatives (Z'=—S-aryl, —S—CH($_n$)aryl($_{3-n}$), n=0–3), and N-sulfonyl derivatives (Z'=—SO$_2$-aryl, —SO$_2$-alkyl). Thiol groups are routinely protected as thioethers (Z"=—CH($_n$)aryl($_{3-n}$), n=1–3, alkyl), thioesters (Z"=acyl), thiocarbonates (Z=—C(=O)—O-alkyl, —C(=O)—O-aryl, —C(=O)—O-alkenyl), thiocarbamates (Z=—C(=O)—NH-alkyl, —C(=O)—NH-aryl, —C(=O)—NH-alkenyl), and disulfides (Z"=—S-alkyl, aryl).

The present invention also encompasses X of the above formula being a "leaving group". Thus, when X is a leaving group in the present invention, it may be chosen from the group consisting of halide (X=—Cl, Br, —I), sulfonate ester (X=—OS(=O)$_2$-alkyl, —OS(=O)$_2$-aryl), activated amino (X=—N(alkyl)$_3$+, N$_2$).

The present invention also encompasses X of the above formula being a "Michael acceptor". Thus, in the present invention X can be chosen from the group consisting of substituents of the formula —O—"MA" or —N(H)$_n$"MA", wherein "MA" is the Michael acceptor of the formula

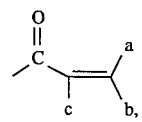

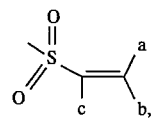

and

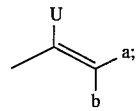

and wherein a, b and c independently can be hydrogen, alkyl, and aryl; and wherein U is chosen from —CH(=O), —C(=O)R, —C(=O)NH$_2$, —CN, —NO$_2$, —S(=O)R, —S(=O)$_2$R, and n is 0 or 1. A preferred Michael acceptor is X=

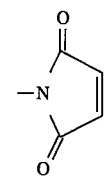

When X is a linking group it is of the formula —O—A—B or —N(H)$_n$—A—B, wherein n=0 or 1 to satisfy the nitrogen valency; and wherein A is a spacer group consisting of from 0 to 50 carbon atoms and heteroatoms, including not more than ten heteroatoms, arranged in a straight or branched chain, saturated or unsaturated, with the provisos that not more than two heteroatoms may be directly linked in the sequence —O—A—B or —N(H)$_n$—A—B, the sequence —O—A—B or —N(H)$_n$—A—B cannot contain —O—O—, that in the sequence —N(H)$_n$—A—B, when n=0, then N—A taken together may comprise a ring of not more that 6 atoms; and that branchings may occur only on carbon atoms; and wherein B is a reactive functional group selected from —C(=O)OH, —NH$_2$, —CH(=O), halo (—Cl, —Br, —I), sulfonate ester(OS(=O)$_2$-alkyl, —OS(=O)$_2$-aryl), Michael acceptor, phosphoramidite, and phosphonate.

The present invention also provides a process for preparing 5 (6) methyl-substituted fluorescein derivatives which comprises (a) protecting the hydroxyls at the 3' and 6' positions of the following formulas III and IV, separately or as a mixture:

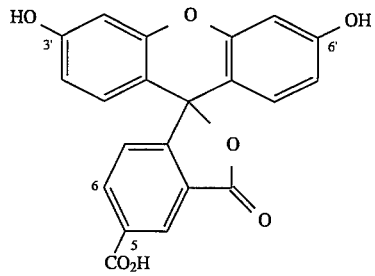
FORMULA III

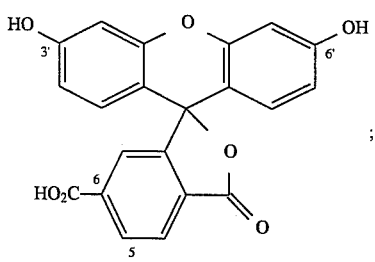
FORMULA IV to yield compounds of the following formula V and VI:

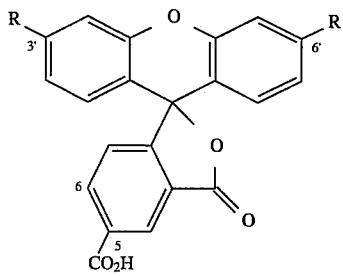
FORMULA V

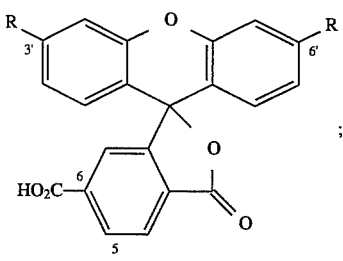
FORMULA VI (b) reducing the carboxylic acid function of compounds of formulas V and VI such as to form compounds of the following formulas VII and VIII:

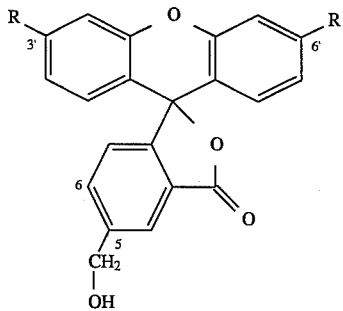
FORMULA VII

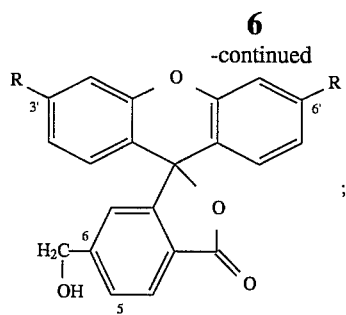
FORMULA VIII (c) when prepared as a mixture, separating the isomers of formulas VII and VIII chromatographically such as to give the pure isomers of formulas VII and VIII;

(d) converting the hydroxyl moiety of the compounds of the formulas VII and VIII to a leaving group, independently or as a mixture such as to give compounds of the formula IX or X:

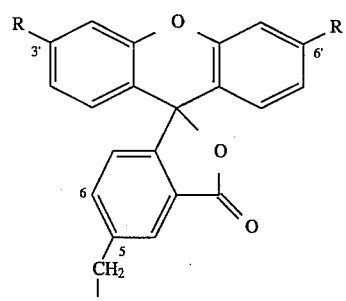
FORMULA IX

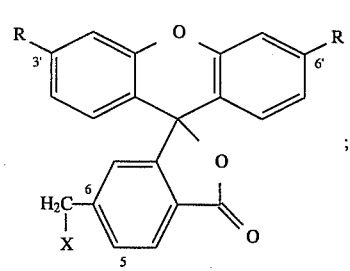
FORMULA X (e) displacing the leaving group X with a nucleophilic "pro" amino, "pro" thiol, or sodium sulfhydride group such as to give compounds of the formulas IX and X:

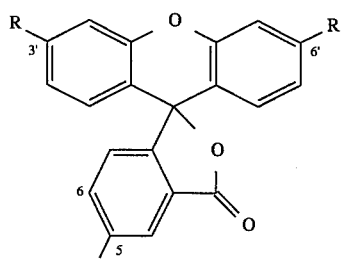
FORMULA XI

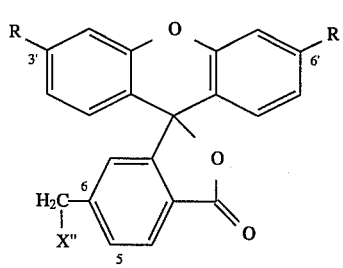
FORMULA XII wherein X''=a "pro" amino, "pro" thiol group, or thiol;

(f) converting the X" groups in compounds of formula XI or XII such as to give compounds of the formulas XIII or XIV

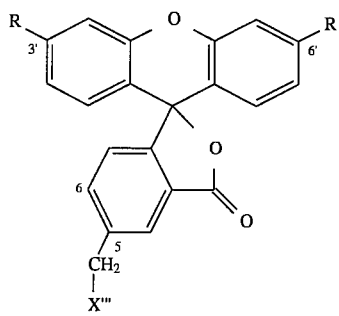
FORMULA XIII

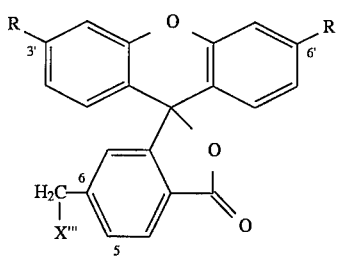
FORMULA XIV wherein X"=NH₂ or SH; and (g) deprotecting the hydroxyl functions at positions 3' and 6' of the compounds of the formulas XIII and XIV such as to give the compounds of the formulas XV or XIV:

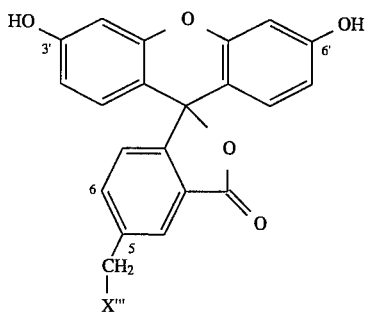
FORMULA XV

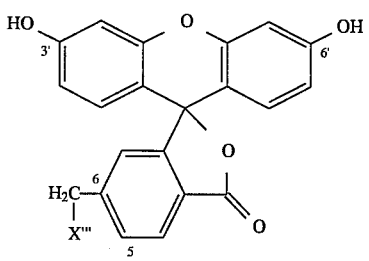
FORMULA XVI wherein X"=NH₂ or SH. The present invention also provides a method for the preparation 5 (6) methyl-substituted fluorescein derivatives which comprises steps a–e above and steps f and g in their inverse order.

The present invention also provides a method for the preparation 5 (6) methyl-substituted fluorescein derivatives which comprises steps a–c, and g above to produce compounds of the formula XVII or XVIII:

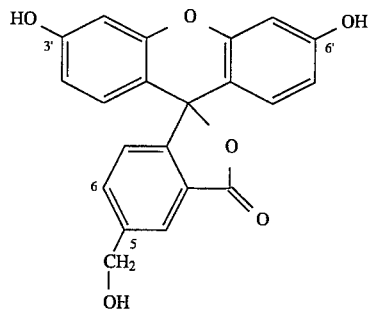
FORMULA XVII

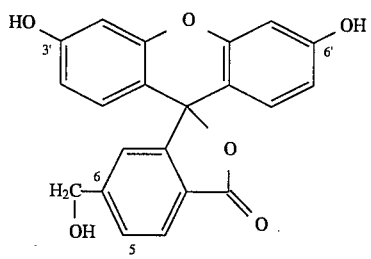
FORMULA XVIII

The terms nucleophilic, "'pro' amino" and "'pro' thiol" include those nitrogen and sulfur containing nucleophiles which are readily converted to amino or thiol groups. Nucleophilic "pro" amino groups are selected from the group

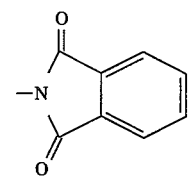

consisting of dicarboximides anions, e.g. phthalimide anion iminodicarbonates anions, e.g., dibenzyliminodicarbonate anion

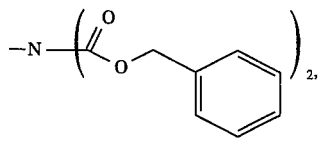

sulfonamide anions: $^-N(H)_n$(alkyl, aryl, alkenyl, acyl)$_{2-n}$ $S(=O)_2$(alkyl, aryl, alkenyl), n=0–2; sulfonimide anions: $^-N(S(=O)_2$(alkyl, aryl, alkenyl))$_2$; O-substituted hydoxylamines: $NH_2O$(alkyl, aryl, acyl); O-substituted hydroxamic acid anions: N(acyl)O(alkyl, aryl, acyl); azide anion: $N_3^-$; cyanide anion: –CN; isocyanate anion: –N=C=O; and isothiocyanate anion: $^-N=C=S$.

"Pro" thiol groups include thiourea: $H_2NC(=S)NH_2$; sodium N,N-diethylthiocarbamate; thiosulfate anion: $S_2O_3^{2-}$; disulfide anion: $S_2^{2-}$.

The present invention also provides for fluorescein conjugates of the formula XIX or XX:

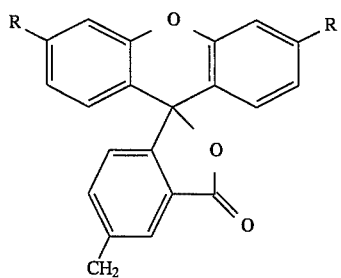
FORMULA XIX or

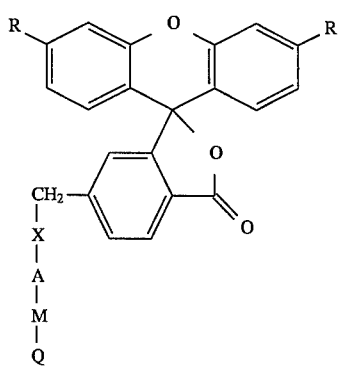
FORMULA XX wherein R is as defined above and X is chosen from the group consisting of —N(H)n—, —O—, or —S—:

wherein n=0 or 1 to satisfy the nitrogen valency;

wherein A is a spacer group consisting of from 0 to 50 carbon atoms and heteroatoms, including not more than ten heteroatoms, arranged in a straight or branched chain, saturated or unsaturated, with the provisos that not more than two heteroatoms may be directly linked in the sequence —X—A—M—Q, the sequence —X—A—M—Q cannot contain —O—O—, that when X=—N(H)$_n$— in the sequence —X—A—M—Q, when n=0 then N—A taken together may comprise a ring of not more that 6 atoms; and that branchings may occur only on carbon atoms;

wherein M is a linking group selected from >C(=O), —NH—, —O—C(=O)—, —N(H)—C(=O)—, —N(H)—C(=S)—, —S—, —P(=O)(O—)—and;

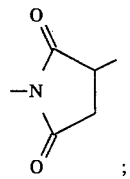

and wherein Q is a conjugation partner.

The present invention also provides methods for detecting the presence an analyte in a test sample, wherein the method comprises the step of contacting the test sample with an indicator reagent which comprises a compounds of the formula XIX or XX.

In addition, the present invention provides test kits which contain an indicator reagent comprising a compound of Formula XIX or XX.

DETAILED DESCRIPTION OF THE INVENTION

Figure 1:
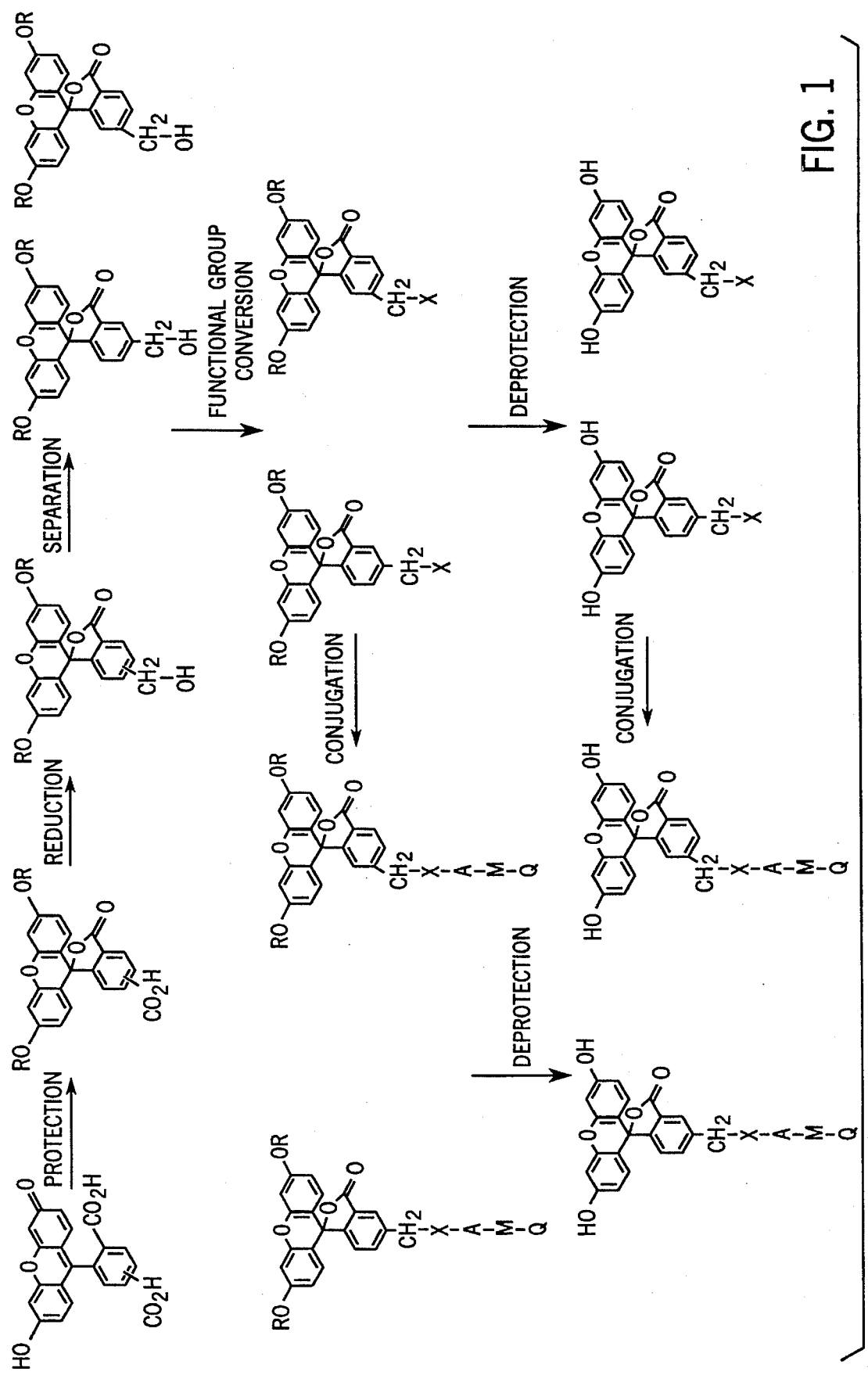
FIG. 1 is a schematic diagram of the process of the invention.

The present invention provides fluorescein derivatives of the following formulas:

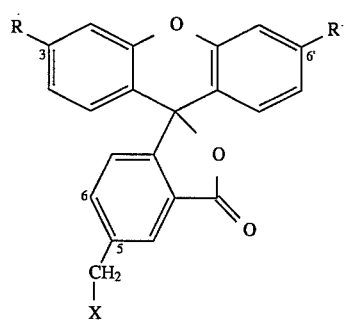
FORMULA I and

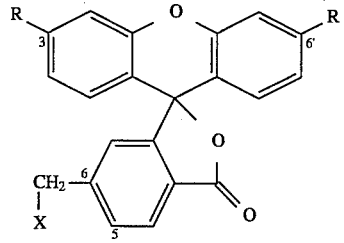
FORMULA II wherein R is selected from the group consisting of hydroxy (—OH), and protected hydroxy (—OZ); and wherein X is selected from the group consisting of hydroxy (—OH), protected hydroxy (—OZ), amino (—NH$_2$), protected amino (—NH$_m$Z'$_{2-m}$), thiol (—SH), protected thiol (—SZ"), a leaving group, a Michael acceptor, phosphoramidite, phosphonate and a linking group.

Protecting groups for hydroxyl, amino and thiol functional groups are well known in the art (T. W. Greene, *Protective Groups in Organic Synthesis*, John Wiley and Sons. New York, 1981). Hydroxyl groups are routinely protected as alkyl or aryl ethers (Z=alkyl, aryl, alkenyl), silyl ethers (Z=silyl), esters (Z=acyl), carbonates (Z=—C(=O)—O-alkyl, —C(=O)—O-aryl, —C(=O)—O-alkenyl) and carbamates (Z=—C(=O)—NH-alkyl, —C(=O)—NH-aryl, —C(=O)—NH-alkenyl). Amino groups are routinely protected as carbamates (Z'=—C(=O)—O-alkyl, —C(=O)—O-aryl, —C(=O)—O-alkenyl), biscarbamates (m=0; Z'=—C(=O)—O-alkyl, —C(=O)—O-aryl, —C(=O)—O-alkeny) amides (Z'=—C(=O)-alkyl, —C(=O)-aryl, —C(=O)-alkenyl), cyclic imides (Z'=phthaloyl), N-benzyl derivatives (Z'=—CH($_n$)aryl($_{3-n}$), n=1-3), imine derivatives (Z'=—CH($_n$)alkyl($_{2-n}$), =CH($_n$)aryl($_{2-n}$) n=0-2), silyl derivatives (Z'=silyl), N-sulfenyl derivatives (Z'=—S-aryl, —S—CH($_n$)aryl($_{3-n}$), n=0-3), and N-sulfonyl derivatives (Z'=—SO$_2$-aryl, —SO$_2$-alkyl). Thiol groups are routinely protected as thioethers (Z"=—CH($_n$)aryl($_{3-n}$), n=1–3, alkyl), thioesters (Z"=acyl), thiocarbonates (Z=—C(=O)—O-alkyl, —C(=O)—O-aryl, —C(=O)—O-alkenyl), thiocarbamates (Z=—C(=O)-NH-alkyl, —C(=O)—NH-aryl, —C(=O)—NH-alkenyl), and disulfides (Z"=—S-alkyl, aryl).

The present invention also encompasses X of the above formula being a "leaving group". A "leaving group" has been defined in the art as follows:.

"In a reaction in which a substrate molecule becomes cleaved, part of it (the part not-containing the carbon) is usually called the leaving group." (J. March, *Advanced Organic Chemistry*, 2nd Ed., McGraw-Hill, New York, 1977, p 187).

Most commonly, halides are the most useful leaving groups in nucleophilic reactions, while alcohols, amines and thiols must be activated prior to reaction. Alcohols are most commonly activated by conversion to sulfonate esters, or halides, or generated in situ by the Mitsunobu reaction; amines by quarternization or diazotization. Thus, when X is a leaving group in the present invention, it may be chosen from the group consisting of halide (X=—Cl, Br, —I), sulfonate ester (X=—OS(=O)$_2$-alkyl,-OS(=O)$_2$-aryl), activated amino (X=—N(alkyl)$_3$+, N$_2$). It should be recognized that one of ordinary skill in the art may determine other leaving groups which also can be utilized in the novel processes of the present invention.

The present invention also encompasses X of the above formula being a "Michael acceptor". A "Michael acceptor" has been defined in the art as follows:

"The nucleophilic addition of enolate (or analogous) anions to the carbon carbon double bond of α,β-unsaturated ketones, aldehydes nitriles or carboxylic acid derivatives, a process known as the Michael reaction. The unsaturated compounds in the reaction, often called Michael acceptors, may include any unsaturated system having a functional group capable of stabilizing the carbanionic intermediate. The Michael acceptors may also add a variety of nucleophiles such as alcohols, thiols, and amines." H. O. House, *Modern Synthetic Reactions*, W. A. Benjamin, Inc., Menlo Park, Calif., 1972, pp. 595–96.

Common functional groups which can activate a double bond to this kind of nucleophilic addition include, —CH(=O), —C(=O)R, —C(=O)NH$_2$, —CN, —NO$_2$, —S(=O)R, —S(=O)$_2$R. Thus, the in the present invention, X can be chosen from the group consisting of groups of the formula —O—"MA" or —N(H)$_n$"MA", wherein "MA" is the Michael acceptor of the formula

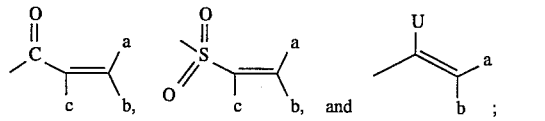

wherein a, b and c independently can be hydrogen, alkyl, and aryl and wherein U is chosen from —CH(=O), —C(=O)R, —C(=O)NH$_2$, —CN, —NO$_2$, —S(=O)R,

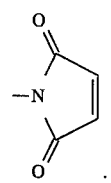

—S(=O)$_2$R, and n is 0 or 1. A preferred Michael acceptor is X=

When X is a linking group it is of the formula —O—A—B or —N(H)$_n$—A—B:

wherein n=0 or 1 to satisfy the nitrogen valency; and wherein A is a spacer group consisting of from 0 to 50 carbon atoms and heteroatoms, including not more than ten heteroatoms, arranged in a straight or branched chain, saturated or unsaturated, with the provisos that not more than two heteroatoms may be directly linked in the sequence —O—A—B or —N(H)$_n$—A—B, the sequence —O—A—B or —N(H)$_n$—A—B cannot contain —O—O—, that in the sequence —N(H)$_n$—A—B, when n=0, then N—A taken together may comprise a ring of not more that 6 atoms; and that branchings may occur only on carbon atoms; and wherein B is a reactive functional group selected from —C(=O)OH, —NH$_2$, —CH(=O), halo (—Cl, —Br, —I), sulfonate ester(OS(=O)$_2$-alkyl, —OS(=O)$_2$-aryl), Michael acceptor, phosphoramidite, and phosphonate.

The present invention also provides a process for preparing 5 (6) methyl-substituted fluorescein derivatives which comprises:

(step a) protecting the hydroxyls at the 3' and 6' positions of compounds of the following formulas III and IV, independently or as a mixture:

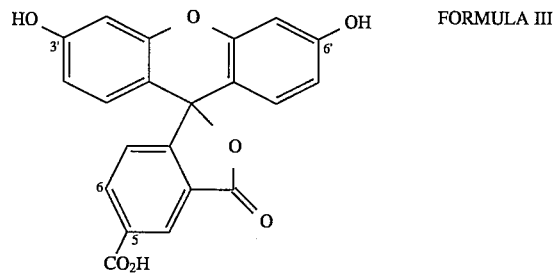

FORMULA III

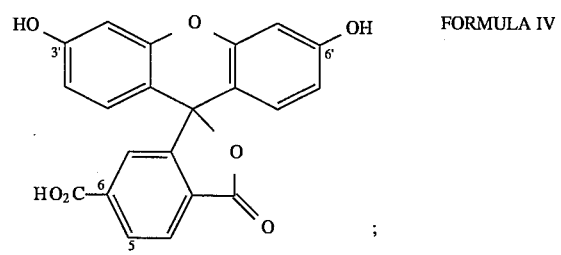

FORMULA IV to yield compounds of the following formula V and VI:

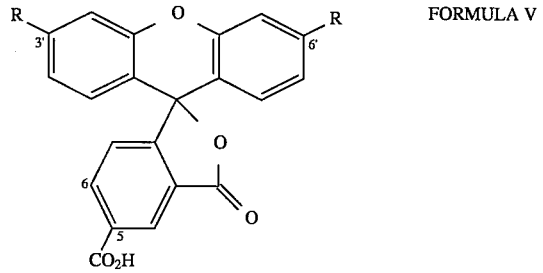

FORMULA V

-continued

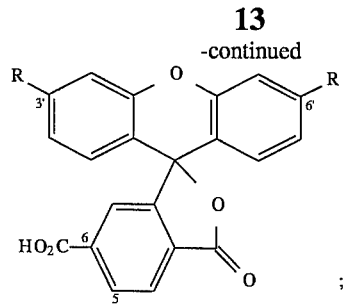
FORMULA VI (step b) reducing the carboxylic acid function of compounds of formulas V and VI such as to form compounds of the following formulas VII and VIII:

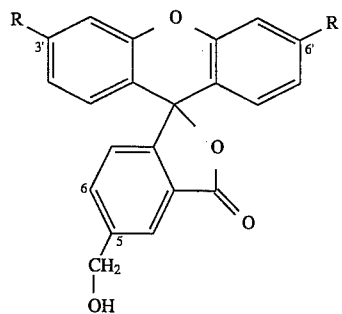
FORMULA VII

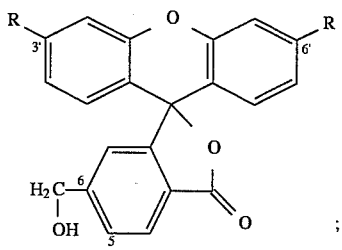
FORMULA VIII (step c) when prepared as a mixture, separating the isomers of formulas VII and VIII chromatographically such as to give the pure isomers of formula VII and VIII;

(step d) converting the hydroxyl moiety of the compounds of the formula VII and VIII to a leaving group, independently or as a mixture, such as to give compounds of the formula IX or X:

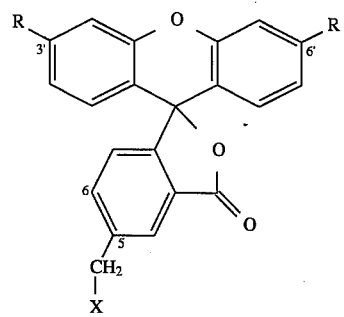
FORMULA IX

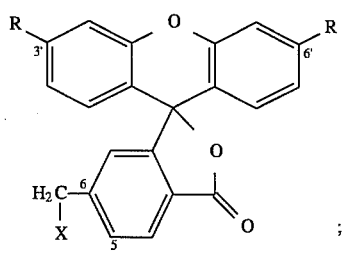
FORMULA X (step e) displacing the leaving group X with a nucleophilic "pro" amino, "pro" thiol, or sodium sulfhydride group such as to give compounds of the formulas:

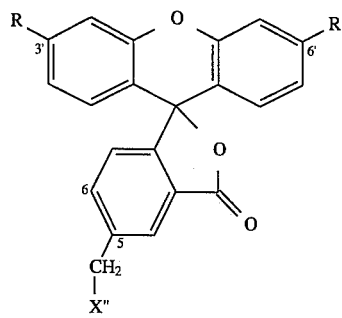
FORMULA XI

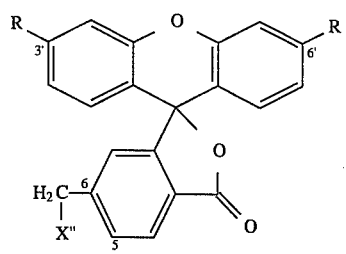
FORMULA XII wherein X"=a "pro" amino, "pro" thiol group, or thiol;

(step f) converting the X" groups in compounds of formula XI or XII such as to give compounds of the formulas XIII or XIV:

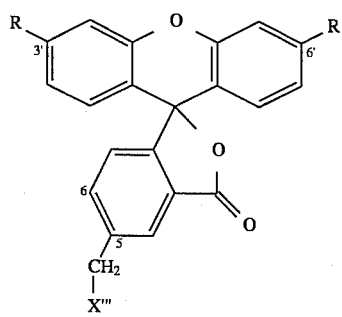
FORMULA XIII

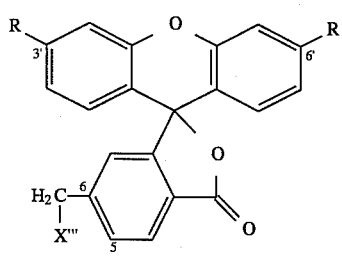
FORMULA XIV wherein X'''=NH$_2$ or SH;

(step g) deprotecting the hydroxyl functions at positions 3' and 6' of the compounds of the formulas XIII and XIV such as to give the compounds of the formulas XV and XVI:

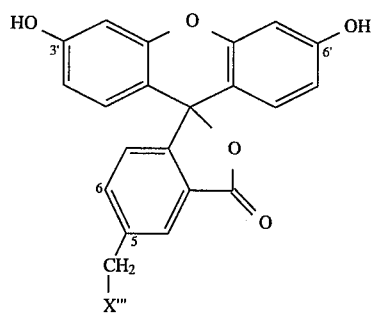

FORMULA XV

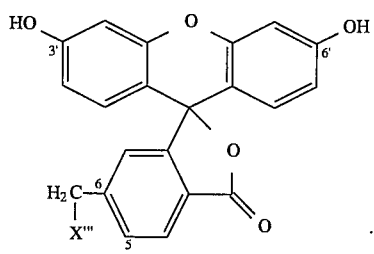

FORMULA XVI

The present invention also provides a method for the preparation 5 (6) methyl-substituted fluorescein derivatives which comprises steps a–e above and steps f and g in their inverse order.

The present invention also provides a method for the preparation 5 (6) methyl-substituted fluorescein derivatives which comprises steps a–c, and g above to produce compounds of the formula XVII and XVIII:

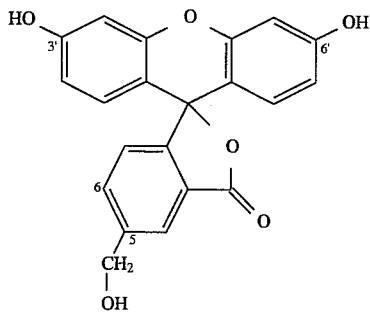

FORMULA XVII

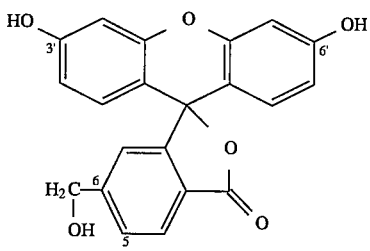

FORMULA XVIII

The terms nucleophilic "'pro' amino" and "'pro thiol'" are herein defined as those nitrogen and sulfur containing nucleophiles known in the art to be readily converted to amino or thiol groups. Nucleophilic "pro" amino groups are commonly chosen from the group consisting of dicarboximides anions, e.g.

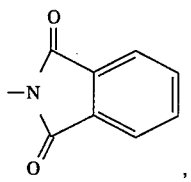

iminodicarbonate anions, e.g.,

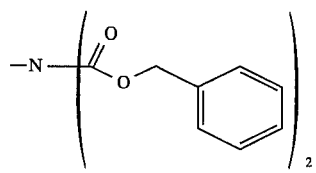

dibenzyliminodicarbonate anion, sulfonamide anions: $^{31}$N(H)$_n$(alkyl, aryl, alkenyl, acyl)$_{2-n}$S($=$O)$_2$(alkyl, aryl, alkenyl), n=0–2; sulfonimide anions: —N(S($=$O)$_2$(alkyl, aryl, alkenyl))$_2$; O-substituted hydoxylamines: NH$_2$O(alkyl, aryl, acyl); O-substituted hydroxamic acid anions: $^-$N(acyl)O(alkyl, aryl, acyl); azide anion: N$_3^-$; cyanide anion: $^-$CN; isocyanate anion: $^-$N$=$C$=$O; and isothiocyanate anion: $^{31}$N$=$C$=$S.

Commonly used "pro" thiol groups include thiourea: H$_2$NC($=$S)NH$_2$; sodium N,N-dimethylthiocarbamate; thiosulfate anion: S$_2$O$_3^{2-}$; disulfide anion: S$_2^{2-}$. It will be recognized that one of ordinary skill in the art may-determine other "pro" amino and "pro" thiol groups which also would work in the novel processes of the present invention.

The present invention also provides for fluorescein conjugates of the following formulas XIX or XX:

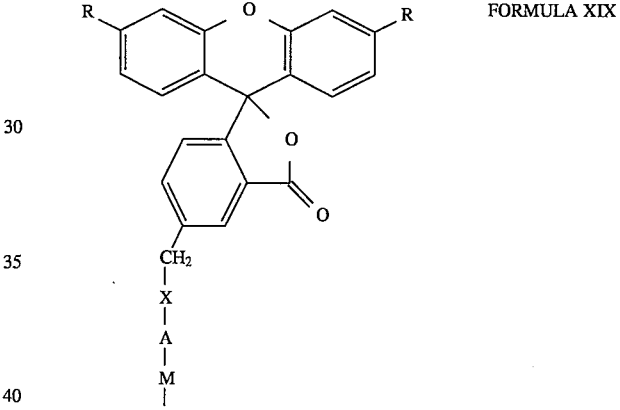

FORMULA XIX or

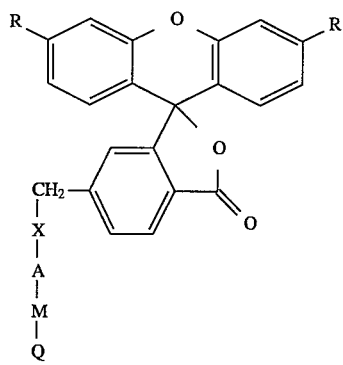

FORMULA XX wherein R is as defined above and X is chosen from the group consisting of —N(H)n—, —O—, or —S—;

wherein n=0 or 1 to satisfy the nitrogen valency;

wherein A is a spacer group consisting of from 0 to 50 carbon atoms and heteroatoms, including not more than ten heteroatoms, arranged in a straight or branched chain, saturated or unsaturated, with the provisos that not more than two heteroatoms may be directly linked in the sequence —X—A—M—Q, the sequence —X—A—M—Q cannot contain —O—O—, that when X=—N(H)n—in the sequence —X—A—M—Q, when n=0 then N—A taken together may comprise a ring of not more that 6 atoms;, and that branchings may occur only on carbon atoms;

wherein M is a linking group selected from >C(=O), —NH—, —O—C(=O)—, —N(H)—C(=O)—, —N(H)—C(=S)—, —S—, —P(=O)(O—)—and ;

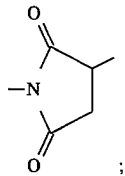

and wherein Q is a conjugation partner.

The present invention also provides methods for detecting the presence an analyte in a test sample, wherein the method comprises the step of contacting the test sample with an indicator reagent which comprises a compounds of the formula XIX or XX.

The starting material, 5(6)-carboxyfluorescein, is available from Eastman Kodak, Rochester, N.Y. A preparation of 3',6'diacetyl-5(6)-carboxyfluorescein previously has been described erroneously as the pure isomer 3',6'-diacetyl-6-carboxyfluorescein, and lacks any characterization of the compound. See, J. W. Bruning et al. *J. Immunological Methods* 33:33–44 (1980). The compounds 5-aminomethyl and 5-bromomethylfluorescein recently have become commercially available from Molecular Probes, Inc., Eugene Oreg. 97492.

An approximately 40:60 mixture of 5(6)-carboxyfluorescein, which exist in both an open form and a closed form, was modified to increase its solubility in organic solvents and to differentiate the two carboxyl groups, by treatment with acetic anhydride. Other means of accomplishing this solubility may be known to those skilled in the art, and could include the acylation of the hydroxyls with a different anhydride, acid halide or active ester, or silylation with any number of silyl halides, or alkylation to give rise to suitable derivatives. Once so treated, the 5(6)-carboxyfluorescein derivative is soluble in organic solvents commonly used for the reduction of carboxylic acid derivatives.

For example the procedure for the conversion of 5(6)-carboxyfluorescein to the diacetylated species followed that of the unsubstituted fluorescein as described by W. R. Orndorff and A. J. Hemmer, "Fluorescein and Some of Its Derivatives", *J. Amer. Chem. Soc.* 49:1272–1280 (1927). Briefly, this procedure involved reaction of 5(6)-carboxyfluorescein in acetic anhydride at reflux with sodium acetate; aqueous workup; and purification of the product mixture, 3',6'-diacetyl-5(6)-carboxyfluorescein, by column chromatography on silica.

The remaining carboxylic acid can be reduced to the alcohol by treatment with borane-tetrahydrofuran complex, borane-dimethylsulfide complex or any other reducing agent selective for carboxylic acids in the presence of esters, over the course of one to two days. A preferred reducing agent is a borane-dimethylsulfide complex.

Alternatively, the carboxylic acid can be converted into the mixed carbonic anhydride with ethyl chloroformate or other active ester and reduced with sodium borohydride ($NaBH_4$) in buffered methanol THF (pH 6.0) for approximately five minutes at 0° C., to the alcohol.

For example 3',6,'diacetyl-5(6)-carboxyfluorescein was converted to 3',6,'diacetyl-5(6)-hydroxymethylfluorescein by both methods previously described herein.

The mixture of alcohols thus formed can be separated conveniently at this stage by column chromatography on silica gel following methods known to those of ordinary skill in the art. For example 3',6,'diacetyl-5(6)-hydroxymethylfluorescein is separated into the pure isomers 3',6,'diacetyl-5-hydroxymethylfluorescein and 3',6,'diacetyl-6-hydroxymethylfluorescein.

The alcohol at this stage can be converted into any of several other derivatives, as is well-known in the art. A preferred derivative was obtained by converting the alcohol into an amine. This was accomplished by converting the hydroxyl into a leaving group and displacing it with a nucleophilic "pro" amino group. Preferred "pro" amino groups are dibenzyl iminodicarbonate and phthalimide. This is conveniently performed under the Mitsunobu conditions, described in 0, Mitsunobu, "The Use of Diethyl Azodicarboxylate and Triphenylphoshpine in Synthesis and Transformation of Natural Products," *Synthesis:*1 (1981).

Briefly, this method involved reaction of 3',6,'diacetyl-5-hydroxymethylfluorescein or 3',6,'diacetyl-6-hydroxymethylfluorescein with diethylazodicarboxylate, triphenylphosphine, and dibenzyl iminodicarbonate or phthalimide in tetrahydrofuran at room temperature under an inert atmosphere; followed by purification by chromatography on silica gel. The subsequent deprotection (removal) of the acetyl groups with basic methanol containing catalytic dimethylaminopryridine, followed by hydrazinolysis of the phthalimide group or acid treatment of the iminodicarbonate group with HBr/acetic acid, gave the 5 or 6-aminomethylfluorescein as the free base or as the hydrobromide salt, respectively.

The fluorescein derivatives of the present invention can be reacted with a variety of conjugation partners such as proteins, peptides, amino acids, DNA-or RNA probe sequences, hormones, steroids, vitamins, drugs, functionalized polymers, both soluble and insoluble, haptens and other chemicals such as polychlorinated biphenyls. The conjugates of the present invention have one of the following general structures of formulas XIX or XX:

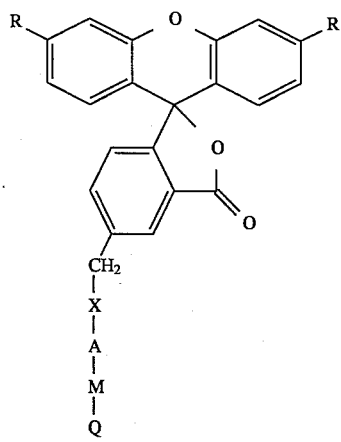

FORMULA XIX or

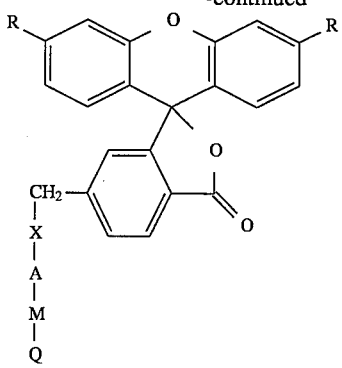

FORMULA XX wherein R is as defined above and X is chosen from the group consisting of —N(H)n—, —O—, or —S—;

wherein n=0 or 1 to satisfy the nitrogen valency;

wherein A is a spacer group consisting of from 0 to 50 carbon atoms and heteroatoms, including not more than ten heteroatoms, arranged in a straight or branched chain, saturated or unsaturated, with the provisos that not more than two heteroatoms may be directly linked in the sequence —X—A—M—Q, the sequence —X—A—M—Q cannot contain —O—O—, that when $X=-N(H)_n$— in the sequence —X—A—M—Q, when n=0 then N—A taken together may comprise a ring of not more that 6 atoms; and that branchings may occur only on carbon atoms;

wherein M is a linking group selected from >C(=O), —NH—, —O—C(=O)—, —N(H)—C(=O)—, —N(H)—C(=S)—, —S—, —P(=O)(O—)— and

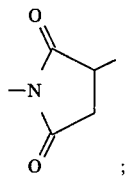

and wherein Q is a conjugation partner.

In the conjugates of the present invention, the chemical bonds between the reactive functional group on the fluorescein derivative and the conjugation partner can be made by a number of methods. It frequently is preferable to form amide bonds. For example, on the fluorescein derivative of Formula I or II ($X=-O-A-B$ or $N(H)_n-A-B$) when B is a carboxyl group, there are several ways to form a bond with amino groups on a conjugation partner using a variety of methods known to those skilled in the art.

Thus, for example, amide bonds am formed by first activating the carboxylic acid moiety of the fluorescein derivative by reaction with an activating reagent such as 1,3-dicyclohexylcarbodiimide and an additive such as N-hydroxysuccinimide. The activated form of the fluorescein derivative then is reacted with the conjugation partner. Alternatively, the carboxylic acid containing fluorescein derivative may be converted, with or without isolation, into a highly reactive mixed anhydride, acyl halide, acyl imidazolide, or mixed carbonate and then combined with the conjugation partner.

Any of these methods results in a derivative of the Formula XIX or XX (—X—A—M—Q) wherein M=—C(=O)—NH—, with the —C(=O)-coming from the fluorescein derivative and the —NH—from the conjugation partner. One of ordinary skill in the art will realize that there are many reagents that can be used to form amide bonds other than those listed herein.

A fluorescein derivative with a terminal amine functionality can be transformed into a highly reactive N-hydroxysuccinimide urethane by reaction with N,N'-disuccinimidyl carbonate in a suitable solvent, such as acetonitrile or dimethylformamide; The resultant urethane then is reacted with the amino groups on the conjugation partner.

A fluorescein derivative with a terminal aldehyde functionality can be coupled to the amino or hydrazide groups on the conjugation partner in the presence of sodium cyanoborohydride, by reductive amination according the methods known to those skilled in the art.

Alternatively, a fluorescein derivative containing a terminal alcohol group can be coupled to the conjugation partner by first reacting it with phosgene or a phosgene equivalent, such as di- or triphosgene or carbonyldiimidazole, resulting in the formation of a highly reactive chloroformate or imidazoloformate derivative (usually without isolation). The resultant active formate ester is then reacted with the conjugation partner.

Alternatively, a fluorescein derivative containing a terminal thiol group can be coupled to the conjugation partner containing a Michael acceptor; or a fluorescein derivative containing a Michael acceptor can react with a conjugation partner that has a-thiol group.

Alternatively, a fluorescein derivative containing a terminal phosphoramidite or phosphonate group can be coupled to the conjugation partner containing a hydroxyl, amino or thiol group.

The so-formed derivatives can be utilized as indicator reagents in a variety of immunoassays for the detection of analytes. "Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances including infectious disease antigens such as viral, bacterial, fungal, rickettsial or other antigens and also cancer markers such as CEA, also macromolecules, haptens and/or their metabolites, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, or the use of lectin as a member of a specific binding pair for the determination of a carbohydrate. The analyte can include a protein, a peptide, an amino acid, DNA or RNA probe sequences, a hormone, a steroid, a vitamin, a drug including those administered for therapeutic purposes as well as those administered for illicit purposes, or other chemicals such as polychlorinated biphenyls, a bacterium, a virus, and metabolites of or antibodies to any of the above substances. The details for the preparation of such antibodies and the suitability for use as specific binding members are well-known to those skilled in the art.

Test samples which can be tested by employing a tracer of the present invention described herein include biological fluids such as human and animal body fluids and non-biological fluids. Examples of biological fluids include whole blood, serum, plasma, milk, cerebrospinal fluid, urine, serum and bodily exudates as well as cell culture supernatants, and the like. Examples of non-biological fluids include water, sledge, etc. Other examples of materials which may be tested include those which contain cells, including both fixed and non-fixed surgical tissue specimens, blood cells, bone marrow, tissue culture cells, and the like.

A "capture reagent", as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a signal generating compound, the tracer of the present invention, which is capable of generating a measurable signal detectable by external means conjugated (attached) to a specific binding member for the analyte(s). "Specific binding member" as used herein means a member of a specific binding pair. That is, two different molecules where one of the molecules through chemical or physical means specifically binds to the second molecule. In addition to being an antibody member of a specific binding pair for the analyte, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to an analyte as in a sandwich assay, to the capture reagent as in a competitive assay, or to the ancillary specific binding member as in an indirect assay.

Solid phases that can be used include a microparticles, both magnetic and non-magnetic, or a mixture of magnetizable polymeric microparticles with chemically or physically bound antigens or antibodies. Polymeric microparticles with chemically or physically bound antigens or antibodies can be used according to the invention as capture phases in a binding reaction to make use of the fast diffusion rates of these particles in solution to yield rapid results Microparticles that can be used according to this invention include polystyrene, carboxylated polystyrene, polymethylacrylate or similar particles with radius in the range of from about 0.1 to 20 μm. Magnetizable microparticles that can be used preferably have ferric oxide or chromium oxide cores and polystyrene, carboxylated polystyrene, polymethylacrylate coating. A preferred separation method for these particles is the use of constant or pulsed magnets, washing said particles, and then suspending the separated particles in a vessel where a signal can be generated and detected. Yet other solid supports are known to those in the art and include the walls of wells of a reaction tray, test tubes, polystyrene beads, nitrocellulose strips, membranes, glass, and others.

It is contemplated that the reagent(s) employed for the assay can be provided in the form of a kit with one or more containers such as vials or bottles, with each container containing a separate reagent such as indicator reagents which comprise the tracers of the present invention as signal generating compounds.

Any assay format which employs a tracer as part of an indicator reagent as a signal generating compound can be utilized. Various examples of assay formats are described herein, and all contemplated will employ the tracer of the present invention as part of the indicator reagent capable of generating a detectable signal. For example, a test sample which may contain the analytes of interest, a mixture of probes for the analytes labeled as described herein and a mixture of capture phases for the analytes are incubated for a period of time and under conditions sufficient to allow optimal immunochemical binding reactions for the analyte to take place. The capture phase then is separated and washed. A substrate specific to the tracer of the invention then is added. After the enzyme/substrate reaction reaches an end point, the separated reaction mixture is stopped. The presence of analyte is determined by detecting the signal generated from the capture phase, and comparing the result obtained to known positive and negative samples.

Ion capture procedures for immobilizing an immobilizable reaction complex with a negatively charged polymer, described in co-pending U.S. patent application Ser. No. 150,278 filed Jan. 29, 1988, which enjoys common ownership and is incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using a tracer of the present invention to produce signal measurements as described in co-pending U.S. patent application Ser. No. 425,643, which enjoys common ownership and is incorporated herein by reference.

It is contemplated that the indicator reagents of the present invention can be utilized in non-solid phase assay systems as well. For example, a test sample suspected of containing an analyte of interest is mixed with a labeled tracer and an antibody specific for the analyte and the tracer is incubated for a time and under suitable conditions for a reaction to occur. Any analyte which may be present in the test sample and the tracer compete for a limited number of binding sites on the antibody, resulting in the formation of analyte-antibody and tracer-antibody complexes. By maintaining constant the concentration of tracer and antibody, the ratio of the formation of analyte-antibody complex to tracer antibody complex is directly proportional to the amount of analyte present in the test sample.

Fluorescence-polarization methods of detection can be used as described herein. Thus, the amount of analyte in the sample is determined by exciting the mixture with polarized light and measuring the polarization of the fluorescence emitted by free tracer and tracer-antibody complexes. A tracer which is not complexed to an antibody is free to rotate in less than the time required for adsorption and re-emission of fluorescent light. As a result, the re-emitted light is relatively randomly oriented such that the fluorescence polarization of a tracer not complexed to an antibody is low, approaching zero. Upon complexing with the specific antibody, the tracer antibody complex thus formed assumes the rotation of the antibody molecule, which is slower than that of the relatively small tracer molecule, thereby increasing the polarization observed. Therefore, when an analyte competes with the tracer for antibody sites, the observed polarization of fluorescence of the tracer-antibody becomes a value somewhere between that of the free tracer and the tracer-antibody complex. If the sample contains a high concentration of the analyte, the observed polarization value is closer to that of the free tracer, i,e, low. If the sample contains a low concentration of the analyte, the polarization value is closer to that of the bound tracer, i.e., high. By sequentially exciting the reaction mixture of an immunoassay with vertically and then horizontally polarized light, and analyzing only the vertical component of the emitted light, the polarization of the fluorescence in the reaction mixture can be accurately determined. The precise relationship between polarization and concentration of the analyte to be determined is established by measuring the polarization values of calibrators having known concentrations. The concentration of the analyte can be interpolated from the standard curve prepared in this manner. This assay is referred to as a homogeneous assay, meaning that the final polarization readings are taken from a solution in which bound tracer is not separated from free tracer.

When using fluorescence polarization, the results can be quantified in terms of "millipolarization units," "span" (in millipolarization units) and "relative intensity." The measurement of millipolarization units indicates the maximum polarization when a maximum amount of the tracer is bound to the antibody in the absence of any analyte in the test sample. The higher the net polarization units, the better the binding of the tracer to the antibody. The "span" is an indication of the difference between the net millipolarization and the minimum amount of tracer bound to the antibody. A larger span provides for a better numerical analysis of the data. The "relative intensity" is a measure of the strength of the fluorescence signal above the background fluorescence. Thus, a higher intensity will give a more accurate measurement. The intensity is determined as the sum of the vertically polarized 1intensity plus twice the horizontally polarized intensity. The intensity can range from a signal of about three times to about thirty times the background noise, depending upon the concentration of the tracer and the other assay variables. Also, the pH at which this method is practised must be sufficient to allow the fluorescein moiety of the tracers to exist in their open form. The pH thus can range from about 4 to 9, preferably from about 6 to 8, and most preferably from about 7 to 7.5, Various buffers can be used to achieve and maintain the pH during the assay procedure. Representative buffers include borate, phosphate, carbonate, Tris, barbital and the like. The choice of a particular buffer is not critical to the practice of this method. Generally, however, Tris-and phosphate buffers are preferred.

The assay method described hereinabove is adaptable to be performed on automated systems such as, but not limited to, the Abbott TD$_x$® Therapeutic Drug Monitoring System, the Abbott AD$_x$™ Abused Drug System, and the Abbott IM$_x$® Fluorescence Polarization Analyzer, all of which are available from Abbott Laboratories, Abbott Park, Ill. 60064.

The present invention will now be described by way of examples, which are meant to illustrate, but not to limit, the spirit and scope of the invention.

EXAMPLES

Example 1

Step a: Acetylation of 5 (6) Carboxyfluorescein

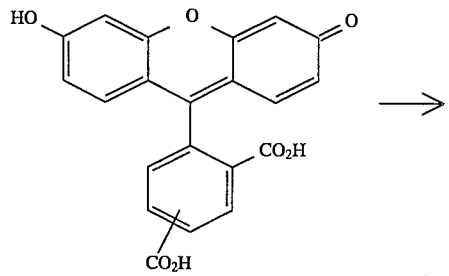

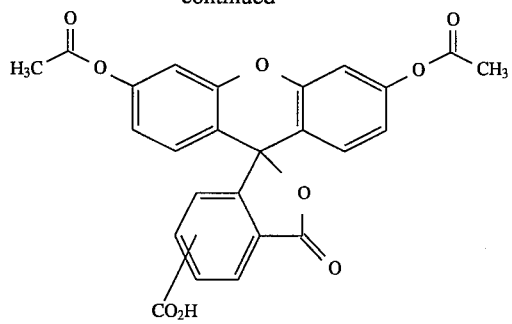

5(6)-Carboxyfluorescein (10g, 27 mmoles) was dissolved in acetic anhydride (200 mL) containing sodium acetate (4.4g, 54 mmoles). The solution was heated to reflux for two (2) hours, allowed to cool to room temperature, and then poured into 1 L water. The mixture was stirred overnight at room temperature, after which the resulting precipitate was collected by filtration, and air dried on the filter for 14 hours at room temperature to give a dark brown solid product. The product was further purified by chromatography on silica gel, eluting with ethyl acetate. The resulting fractions which contained the pure product were combined and evaporated to dryness under reduced pressure. The resulting solid residue was recrystallized from ether/hexanes to give 7.8 g of 3'-6'-diacetyl 5(6)-carboxyfluorescein.

Example 2

Step b,c: Reduction-of 3'-6'-Diacetyl 5(6)-carboxyfluorescein

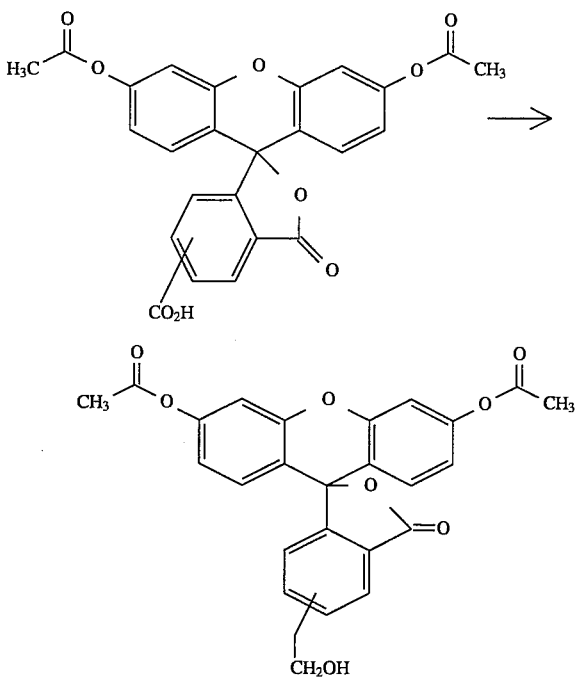

3'-6'-Diacetyl 5(6)-carboxyfluorescein (0.5 g, 1.1 mmoles) was dissolved in tetrahydrofuran (THF) (5 mL), cooled to 0°–5° C., and treated with triethylamine (153 mL, 1.1 mmoles) and ethyl chloroformate (103 mL, 1.1 mmoles) under a nitrogen atmosphere, to form a reaction mixture. The reaction mixture was stirred for 1 hour, and then the reaction mixture was filtered. The resulting filtrate was added to cold sodium phosphate buffer (pH 6.0, 3 mL, 1M), then treated with sodium borohydride (83 mg, 2.2 mmoles) in of water (1 mL). After 5 minutes, the reaction mixture was diluted with water (50 mL) and extracted with ethyl acetate (50 mL). This extraction step was performed twice. The combined extracts were dried over sodium sulfate and evaporated to dryness to give 0.4 g of 3'-6'-diacetyl 5(6)-hydroxymethylfluorescein. The mixture of isomers was further purified and separated on silica gel (60 g), eluting with a mixture of methylene chloride and methyl t-butyl ether at a ratio of 9:1. The first eluting compound was 3'-6'-diacetyl-6-hydroxymethylfluorescein. Calculated mass for $C_{25}H_{19}O_8$: 447.1080; found: 447.1075. The second eluting compound was 3'-6'-diacetyl-5-hydroxymethylfluorescein. Calculated mass for $C_{25}H_{19}O_8$: 447.1080; found: 447.1075.

Example 3

Step d: Conversion of 3'-6'-diacetyl 5 (6)-hydroxymethylfluorescein to 5 (6)-phthalimidomethylfluorescein A mixture of 3',6,'-Diacetyl 5(6)-hydroxymethylfluorescein (90 mg, 0.2 mmoles) was dissolved in THF and treated with phthalimide (30 mg, 0.2 mmoles), triphenylphosphine (53 mg, 0.2 mmoles) and diethyl azodicarboxytate (DEAD) (32 mL, 0.2 mmoles) under a nitrogen atmosphere to form a reaction mixture. The reaction mixture was stirred for 30 minutes, and then the reaction mixture was evaporated to dryness. The residue was Chromatographed on silica [(Chromatotron™, Harrison Research, Palo Alto, Calif.), 2 mm plate, ethyl acetate and hexanes [1:1], at a rate of 10 mL/minute]. Further purification of the resulting product was accomplished by chromatography, by again eluting with methylene chloride and ether (9:1) to give 3',6,'-diacetyl 5(6)-phthalimidomethylfluorescein (90 mg).

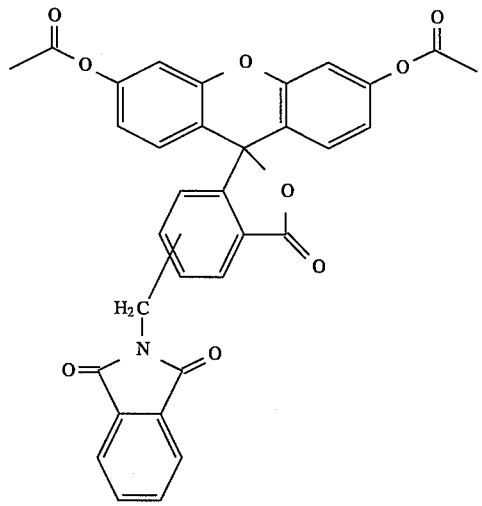

Step e-g: Conversion of 3',6,'-diacetyl 5(6)-phthalimidomethylfluorescein to 5(6)-aminomethylfluorescein.

Example 4

Step e-g: Conversion of 3',6'-diacetyl 5(6)-phthalimidomethylfluorescein to 5(6)-aminomethylfluorescein.

3',6,'-diacetyl 5(6)-phthalimidomethylfluorescein (90 mg) was dissolved in methanol (1 mL) containing aqueous sodium hydroxide (0.1N). After two (2) hours, hydrazine hydrate (100 mL) was added, and the resulting reaction mixture was stirred for another two (2) hours. At the end of that time, the reaction mixture was evaporated to dryness as described previously in Examples 1 and 2. The residue was taken up in methanol (5 mL) containing three drops of methanolic HCl (3N). Ether (50 mL) was added; and on cooling, 5(6)-aminomethylfluorescein precipitated as the hydrochloride salt and was collected by filtration.

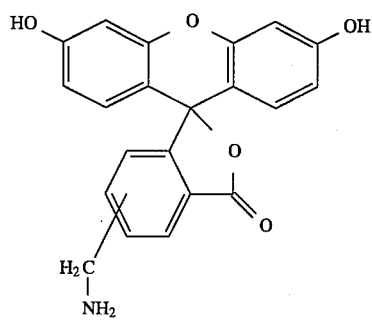

Example 5

Preparation of 3',6'-diacetyl-6-[(N-diCbz-amino)methyl]fluorescein

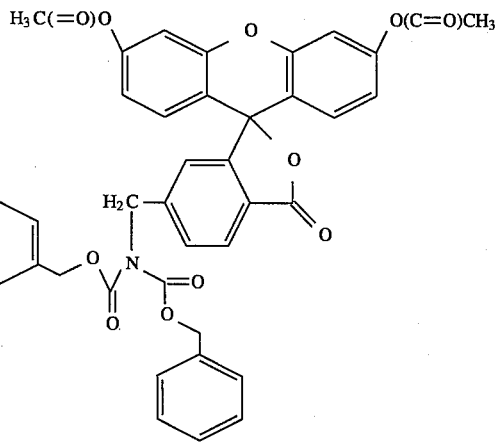

3',6'-Diacetyl-6-hydroxymethylfluorescein (1 g, 2.2 mmol), triphenylphosphine (690 mg, 2.6 mmol), and dibenzyl iminodicarbonate (640 mg, 2.2 mmol) were stirred in THF (50 mL, from benzophenone potassium ketyl) under a nitrogen atmosphere. To this solution was added diethyl azodicarboxylate (415 mL, 2.6 mmol) in THF (25 mL) dropwise over 30 min. After additional stirring for 1 h, the solution was evaporated and the residue purified by filtration through silica gel by eluting with methylene chloride/ether (9:1) to give 3',6'-diacetyl-6-[(N-diCbz-amino)methyl]fluorescein (923 mg, 1.3 mmol, 59%). Calculated mass for $C_{41}H_{32}NO_{11}$: 714.1975; found: 714.1977.

Example 6

Preparation of 3',6,'-diacetyl-5-[(N-diCbz-amino)methyl]fluorescein

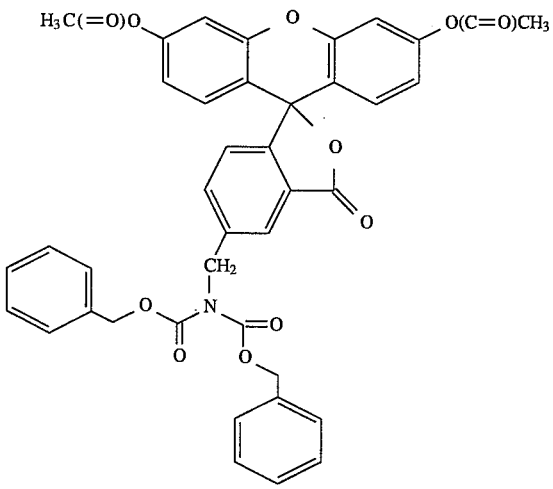

3',6'-diacetyl-5-[(N-diCbz-amino)methyl]fluorescein was prepared from 3',6'-diacetyl-5-hydroxymethylfluorescein in the same manner as Example 5. (1 g, 1.4 mmol, 61%). Calculated mass for $C_{41}H_{32}NO_{11}$: 714.1975; found: 714.1977.

Example 7

Conversion of 3',6'-diacetyl-6-[(N-diCbz-amino)methyl]fluorescein to 6-Aminomethylfluorescein (A) 3',6,'-diacetyl-6-[(N-diCbz-amino)methyl]fluorescein (675 mg, 0.95 mmol) from example 5, was stirred at reflux in methanol (50 mL) containing dimethylaminopyridine (10 mg) for 24 h. The solvent was evaporated to give 6-[(N-diCbz-amino)methyl]fluorescein. Calculated mass for $C_{37}H_{28}NO_9$: 630.1764; found: 630.1763.

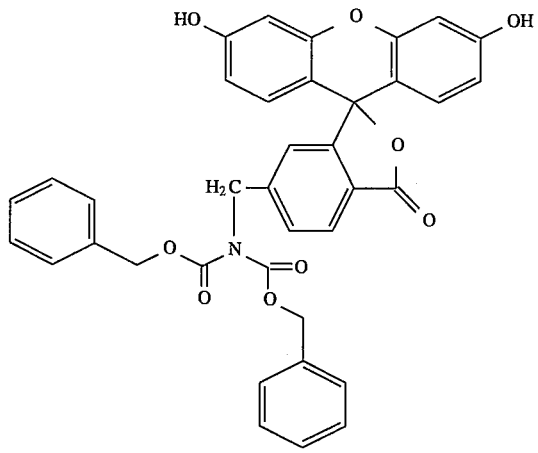

(B) Without further purification 6-[(N-diCbz-amino)methyl]fluorescein was dissolved in methylene chloride (50 mL, from $P_2O_5$) and treated with HBr/HOAc (31%, 5 mL). After stirring for 4 h the reaction mixture was filtered and the precipitate dried in vacuo for 12 h to give 6-aminomethylfluorescein (410 mg, 0.93 mmol, 98%) as the hydrobromide salt.

Calculated mass for $C_{21}H_{16}NO_5$: 362.1028; found: 362.1027.

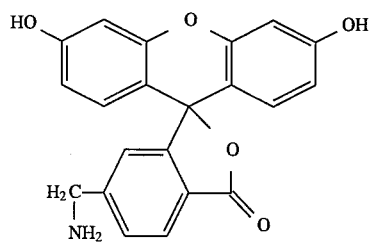

Example 8

Conversion of 3',6'-diacetyl-5-[(N-diCbz-amino)methyl]fluorescein to 5-Aminomethylfluorescein (A) 5-[(N-diCbz-amino)methyl]fluorescein was prepared from 3',6,'-diacetyl-5-[(N-diCbz-amino)methyl]fluorescein (1 g, 1.4 mmol) example 6, by the procedure used in example 7A.

Calculated mass for $C_{37}H_{28}NO_9$: 630.1764; found: 630.1763.

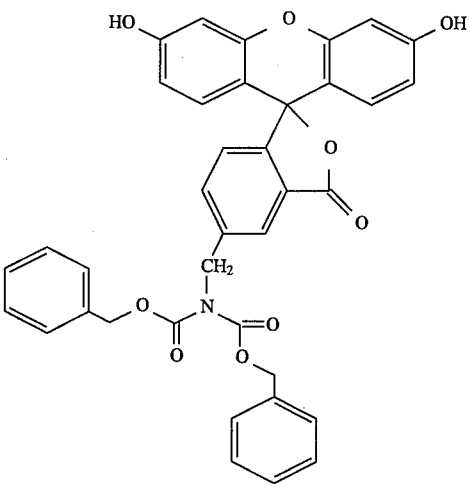

(B) 5-Aminomethylfluorescein (600 mg, 1.36 mmol, 98%) was prepared from 5-[(N-diCbz-amino)methyl]fluorescein as in Example 7B. Calculated mass for $C_{21}H_{16}NO_5$: 362.1028; found: 362.1027.

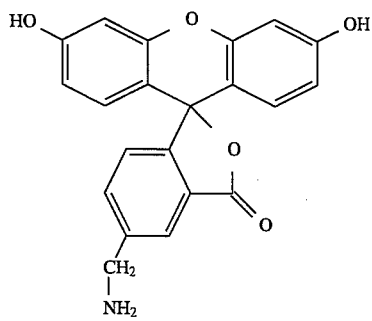

Example 9

Preparation of 5(6)-(maleimido)methylfluorescein

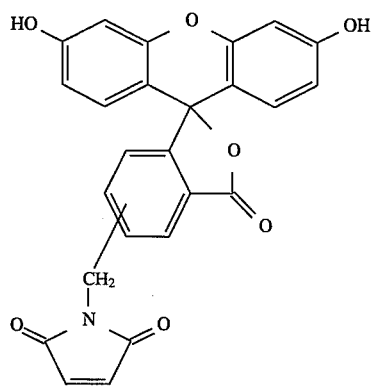

(A) 3'-6'-Diacetyl-5(6)-hydroxymethylfluorescein(100 mg, 0.2 mmoles), maleimide (20 mg, 0.2 mmoles), and triphenylphosphine (57 mg, 0.2 mmoles) were dissolved in THF (10 mL). Diethylazodicarboxylate (40μL, 0.2 mmoles) was added. The reaction was stirred for 24 hours under a nitrogen atmosphere. The reaction mixture was evaporated to dryness in vacuo, and purified by chromatography [(Chromatotron™, Harrison Research, Palo Alto, Calif.), 2 mm plate, methylene chloride and methyl t-butyl ether [9:1], at a rate of 10 mL/minute]. to give 3',6,'-diacetytl-5(6 )-(maleimido)methylfluorescein.

(B) 3',6,'-Diacetytl-5(6)-(maleimido)methyl]fluorescein was treated according to the procedure of Example 7A to give 5(6)-(maleimido)methylfluorescein.

It is contemplated that the invention will be used for the preparation of fluorescein labeled haptens, proteins, nucleotides, nucleotides, oligonucleotides, polymers, solid phases, etc. 5-and 6-Aminomethylfluorescein is a component of several FPIA tracers useful in assays. One skilled in the art will appreciate the above-described fluorescein derivatives and processes can be used under varied conditions to achieve optimum sensitivity and speed.

What is claimed is:

1. A test kit for detecting the presence of at least one analyte in a test sample which comprises a container containing an indicator reagent comprising a compound of formula XIX or XX:

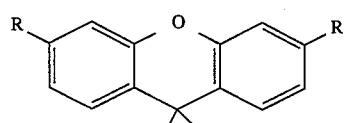

FORMULA XIX or

FORMULA XX wherein R is selected from the group consisting of hydroxy and protected hydroxy, and X is chosen from the group consisting of —N(H)n—, —O—, —S—;

wherein n=0 or 1, to satisfy the nitrogen valency;

wherein A is a spacer group consisting of from 0 to 50 carbon atoms and heteroatoms, including not more than ten heteroatoms, arranged in a straight or branched chain, saturated or unsaturated, with the provisos that:

(a) not more than two heteroatoms may be directly linked in the sequence —XAMQ;

(b) the sequence —XAMQ cannot contain —O—O—, and (c) in the sequence —XAMQ when X=N(H)n—, when n=0, then N—A taken together may comprise a ring of not more than 6 atoms: and (d) that branchings may occur only on carbon atoms; and wherein M is a linking group selected from >C(=O), —NH—, —O—C(=O), —N(H)—C(=O)—, —N(H)—C(=S)—, —S—, —P(=O)(O—)—and

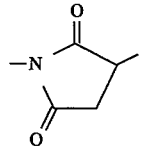

and wherein Q is a conjugation partner.

* * * * *